US00PP20612P2

(12) United States Plant Patent
Terpening

(10) Patent No.: US PP20,612 P2
(45) Date of Patent: Dec. 29, 2009

(54) ***HOSTA* PLANT NAMED 'CLOVELLY'**

(50) Latin Name: ***Hosta* hybrid (Tratt.)**
Varietal Denomination: Clovelly

(76) Inventor: Kent A. Terpening, 5087 Jennifer Dr., North Syracuse, NY (US) 13212-1008

( * ) Notice: Subject to any disclaimer, the term of this patent is extended or adjusted under 35 U.S.C. 154(b) by 0 days.

(21) Appl. No.: 12/221,261

(22) Filed: Aug. 1, 2008

(51) Int. Cl.
*A01H 5/00* (2006.01)

(52) U.S. Cl. ..... Plt./353

(58) Field of Classification Search ..... Plt./353
See application file for complete search history.

*Primary Examiner*—Annette H Para

(57) ABSTRACT

A new and distinct cultivar of ornamental *Hosta* plant named 'Clovelly' with heavily sinuate green leaves, deeply impressed veins, light lavender flowers well above foliage and matching bracts, suitable as a potted plant, for the garden, and for cut flower arrangements.

2 Drawing Sheets

Botanical classification: *Hosta* hybrid (Tratt.)
Variety denomination: 'Clovelly'.

BACKGROUND AND ORIGIN OF THE PLANT

The present invention relates to the new and distinct *hosta* plant, *Hosta* 'Clovelly' discovered by Kent A. Terpening in North Syracuse, N.Y. as the result of a self crossing of *Hosta* 'Split Decision' (not patented). The plant has been successfully asexually propagated by tissue culture methods at a nursery in Zeeland, Mich. and found to be stable and produce identical plants that maintain the unique characteristics of the original plant.

SUMMARY OF THE PLANT

*Hosta* 'Clovelly' differs from its parent, 'Split Decision', as well as all other *hostas* known to the applicant. The most similar known *hosta* cultivars: 'Niagara Falls' (not patented), 'Candy Dish' (not patented) and 'Split Decision' (not patented) are all green cultivars with sinuate margins. 'Niagara Falls' has a cascading habit and is larger in both habit and leaf size. 'Split Decision' has more drawn out and pointed leaf apex with a smaller ratio of leaf width to leaf length. 'Candy Dish' has shiny upper and lower leaf surfaces and is smaller in habit and leaf size and larger ratio of width to length. 'Clovelly' has a matte upper surface texture, a slightly shiny lower leaf surface, and the leaves are more horizontal than 'Niagara Falls'. *Hosta* 'Clovelly' has a longer drawn-out leaf apex (more sharply pointed) than 'Candy Dish' and 'Niagara Falls', but less pointed than 'Split Decision'. *Hosta* 'Clovelly' has a sinuate margin similar to 'American Icon' U.S. Plant Pat. No. 17,441, but the new plant is smaller and is solid green.

There are over 3,600 cultivars registered with The American *Hosta* Society, which is the International Cultivar Registration Authority for the genus *Hosta*. *Hosta* 'Clovelly' differs from these and all unregistered cultivars known to the inventor in that it has:

1. Rich green foliage with deeply undulated margins creating a sinuate edge;
2. Compact habit, medium-sized clumps;

3. Tightly clustered flowers on scapes above foliage high enough for each medium lavender flower to be effectively displayed, each flower subtended by a bract with light lavender center accenting and closely matching the flower color.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
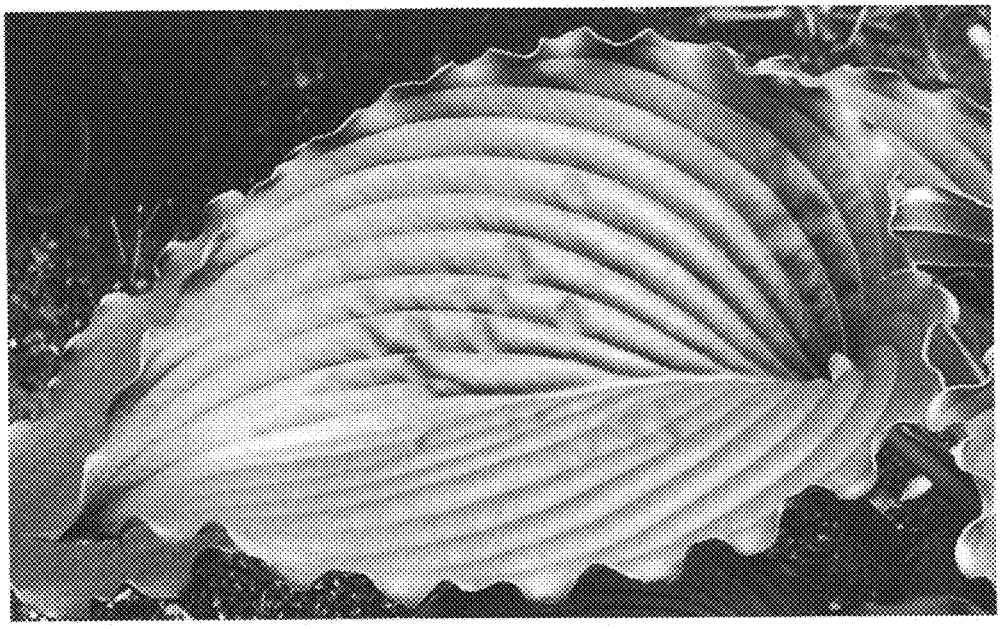
FIG. 1 shows a foliage close-up with intensely sinuate and deeply impressed veins
Figure 2:
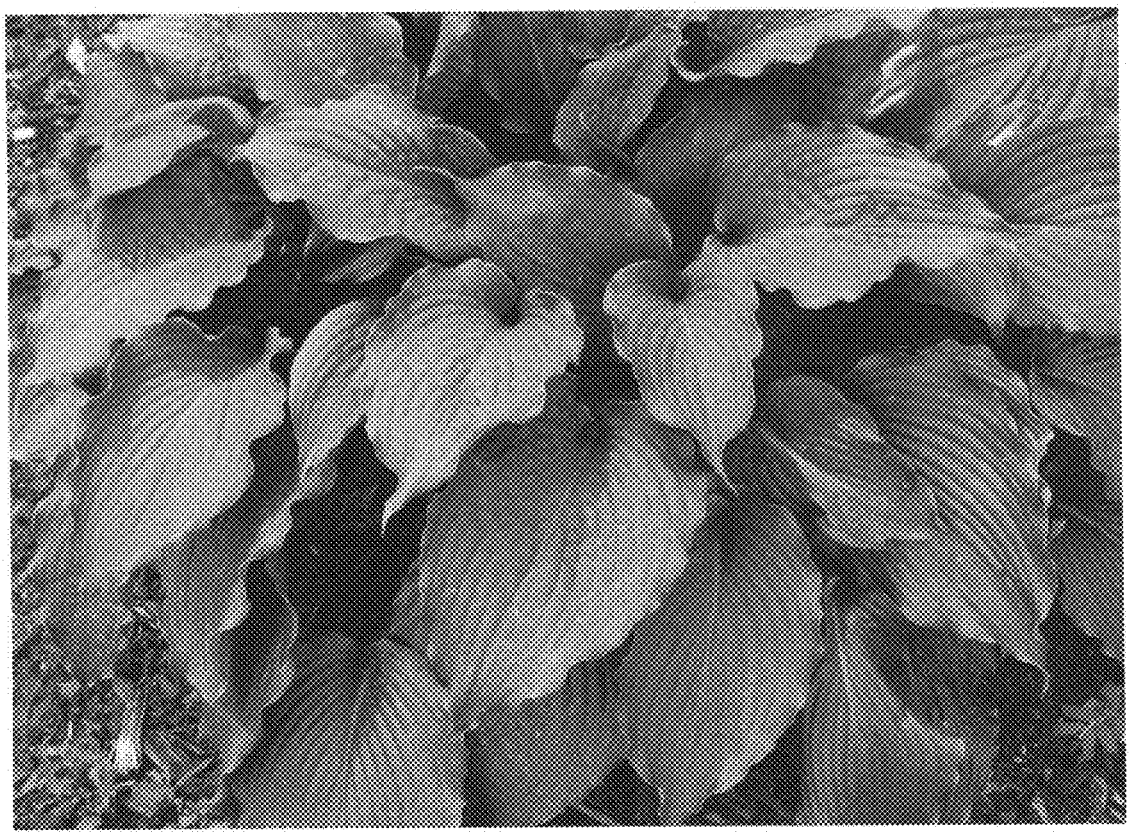
FIG. 2 shows the plant in midseason.
Figure 3:
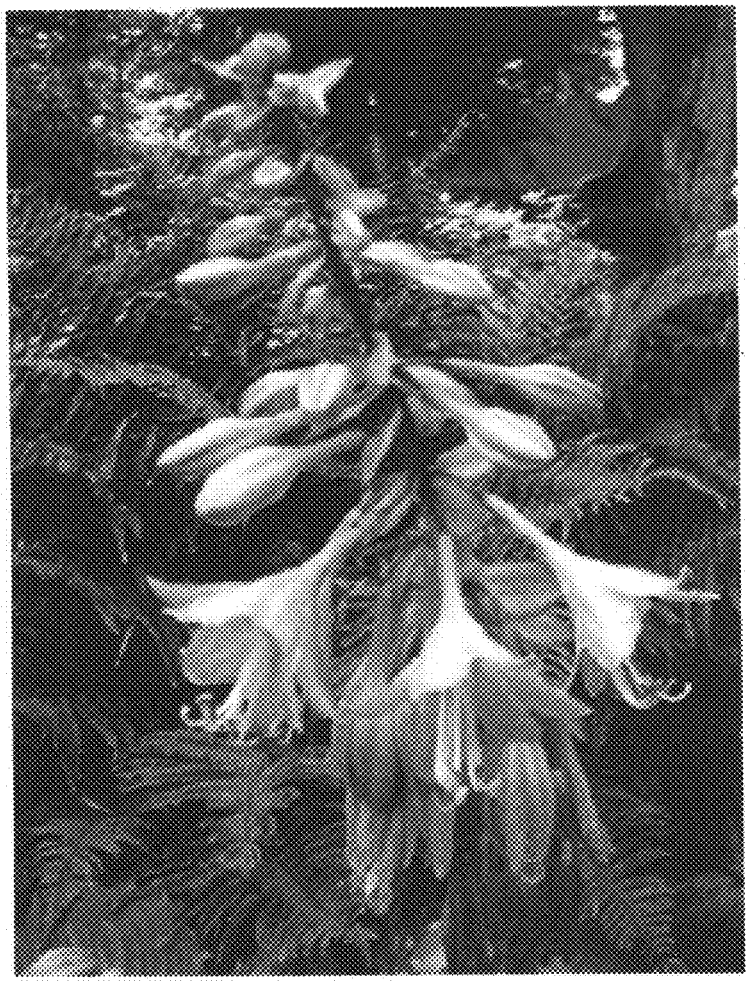
FIG. 3 shows the foliage flower scape.
Figure 4:
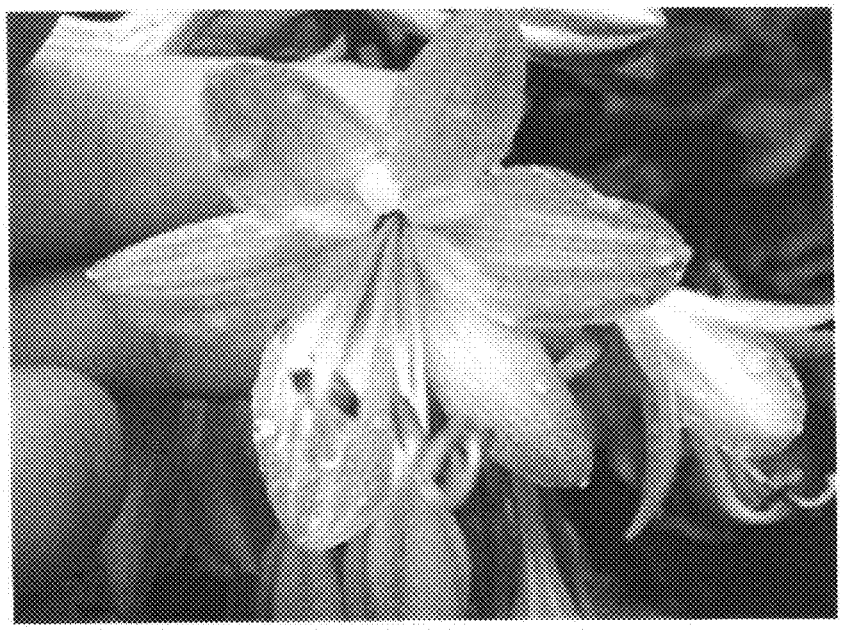
FIG. 4 shows a close-up of the flower with white star pattern.

The following descriptions and color references are based on the 2001 edition of The Royal Horticultural Society Colour Chart except where common dictionary terms are used. The new plant, *Hosta* 'Clovelly', has not been observed under all possible environments. The phenotype may vary slightly with different environmental conditions, such as temperature, light, fertility, moisture and maturity levels, but without any change in the genotype. The following observations and size descriptions are of a three-year old plant in a garden in Zeeland, Mich. under light artificial shade canopy with supplemental water and fertilizer.

Botanical classification: *Hosta* hybrid.

Parentage: *Hosta* 'Split Decision' (not patented) times 'Split Decision'.

Propagation method: By sterile laboratory tissue culture division and garden division.

*Time to initiate roots from tissue culture.*—About three weeks.

Rooting habit: Normal, fleshy, lightly branching.

Plant description:

*Plant shape and habit.*—Hardy herbaceous mound forming perennial with basal rosette leaves, usually bilateral and radially symmetrical, spreading by rhizomes.

*Crop time.*—Summer growing 10 to 15 weeks to finish in a one-liter container; vigor is good.

*Plant size.*—Foliage height at flowering is about 38 cm tall from soil line to the top of the leaves and about 80 cm wide at soil line.

Foliage description:

*Leaf blade.*—Cordate leaf base with acute apex, 12 to 15 cm long, 7 to 8 cm wide, average 14 cm long by 7 cm wide; symmetrical; entire margin with sinuate undulations of about 1.5 cm; 9 to 11 pairs of major parallel deeply impressed veins; top surface begins season slightly glaucous becoming dull matte surfaced, and bottom surface is slightly shiny.

*Blade color.*—Adaxial (top) between RHS 137A and RHS 137B; abaxial (underside): closest to RHS 138A. The 9 to 11 vein pairs on either side of midrib are the color is the same as the surrounding leaf tissue on both the top and bottom of the leaf; midrib on abaxial side is lighter than RHS 138D toward base of leaf becoming RHS 138A toward apex; midrib on adaxial side is RHS 144A in the one third closest to the base developing to RHS 137 A in the one third nearest the apex. PetiolesL 20 to 25 cm long, 8 to 10 mm wide, average 22 cm long and 9 cm wide; RHS 144A in the center adaxial surface and RHS 137A on the edges; RHS 138D in the center abaxial surface and RHS 137A on the edges.

Flower description:

*Buds.*—Clavate with bluntly acute apex and longer thin base; one day prior to opening with longitudinal stripes closest to RHS 79B and lighter than RHS 84D; about 4.5 cm long, and 1.5 cm wide at the broadest portion.

*Flowers.*—30 to 40 per scape; funnelform; 2.5 to 2.8 cm wide and 4.5 to 5.0 cm long, (distal flowers opening smaller), persists open for a normal period, usually one day on or cut from plant; scapes remain effective from mid July into mid August; no detectable fragrance.

*Tepal.*—Two sets of three fused at the base; clavate with acute apex; entire; approximately 4 cm long and 1.4 cm wide; coloring of both sets identical; between RHS 92C and RHS 92D on the inside with the basal one third margin whiter than RHS 92D producing a central, white, five-pointed star pattern; outside between RHS 92C and RHS 92D toward the apex and intensifying to RHS 92B toward base; margins entire margins.

*Pedicel.*—Approximately 8 mm long, 2 mm wide, between RHS 138C and RHS 138 B with violet undertones.

*Peduncle.*—Usually one per division, erect to slightly arching, about 60 cm tall and 0.6 cm diameter, RHS N138B with undertones closest to RHS N77C.

*Gynoecium.*—Single; Style: 5.5 to 5.8 cm long, 1 mm diameter, curled at distal end, lighter than RHS 192D; Stigma: 1 mm to 2 mm in diameter, lighter than RHS 192D.

*Androecium.*—Filaments: six, less than 1 mm in diameter and 5.0 cm long lighter than RHS 192D; Anthers: about 3 mm long and 1.0 mm wide, closest to RHS N92C; Pollen: elliptical, less than 0.1 mm long, nearest RHS 15 B.

*Bracts.*—Lower bracts before flowers sessile with acute apex, protruding upward about 80 degree angle away from scape; lowest up to 3 cm long and 1.2 cm wide before first flower, progressively decreasing in both length and width; Color both surfaces: center between RHS 85A and RHS 85B, lightening to RHS 85D near white.

*Fruit.*—Tri-dehiscent capsule, about 4 cm long and 7 mm wide, nearest RHS 138B.

*Seeds.*—Single winged drupe, about 6 mm long and 4 mm wide, black between RHS 200A and RHS 202A.

Disease resistance: Resistance beyond that of other *hostas* has not been observed. The plant grows best with plenty of moisture and adequate drainage, but is able to tolerate some flooding and drought when mature. Hardiness at least from USDA zone 3 through 9, and other disease resistance is typical of that of other *hostas*.

I claim:

1. A new and distinct cultivar of ornamental *Hosta* plant named 'Clovelly' as herein described and illustrated, with heavily sinuate green leaves, deeply impressed veins, light lavender flowers and matching bracts, suitable as a potted plant, for the garden, and for cut flower arrangements.

* * * * *